(12) United States Patent
Gibson (10) Patent No.: US 7,884,336 B2
(45) Date of Patent: Feb. 8, 2011

(54) SPONGE SANITIZING ENCLOSURE

(76) Inventor: Brent Gibson, 1224 Lincoln Blvd. #5, Santa Monica, CA (US) 90401

( * ) Notice: Subject to any disclaimer, the term of this patent is extended or adjusted under 35 U.S.C. 154(b) by 394 days.

(21) Appl. No.: 12/215,897

(22) Filed: Jul. 1, 2008

(65) Prior Publication Data

US 2010/0003175 A1 Jan. 7, 2010

(51) Int. Cl.
*G01N 23/00* (2006.01)
*H01J 37/20* (2006.01)

(52) U.S. Cl. .............. 250/455.11; 250/454.11; 250/453.11; 250/504 R; 422/24; 422/300; 15/4; 15/28; 15/29; 15/97.1; 15/104.93; 15/104.94; 15/208; 15/311; 15/246.3; 34/275

(58) Field of Classification Search ............ 250/455.11, 250/454.1, 453.11, 504 R; 422/24, 300; 15/4, 28, 29, 97.1, 104.93, 104.94, 208, 311, 15/246.3; 34/275
See application file for complete search history.

(56) References Cited

U.S. PATENT DOCUMENTS

2006/0255291 A1* 11/2006 Harris ............... 250/455.11
2007/0075268 A1* 4/2007 Harris ............... 250/455.11

FOREIGN PATENT DOCUMENTS

WO WO 2004/031706 A1 * 4/2004

* cited by examiner

*Primary Examiner*—Jack I Berman
*Assistant Examiner*—Meenakshi S Sahu (57) ABSTRACT

Sponge sanitizing enclosure with a front cover, a rear cover, an inner back plate, a base housing, a push plate, a push button, a UV lamp, electronics to support the UV lamp, a battery power supply, a translucent sponge, and a hinge member. The front and rear cover each being dish shaped and forming a hollow housing and being joined at their base by the hinge member. The inner back plate forms a bisection of the front cover and the rear cover. The UV light is located between the rear cover and the inner back plate. The front cover includes a centrally located aperture that accepts the push button which is fixedly attached to the push plate. The space between the push plate and the inner back plate accommodates the translucent sponge. The base housing encloses the electronics and the battery power supply that support the UV lamp.

7 Claims, 7 Drawing Sheets

SPONGE SANITIZING ENCLOSURE

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of portable storage enclosures and more specifically to a sponge sanitizing enclosure.

During the course of cleaning surfaces in the kitchen or other areas of a home or workplace, one frequently uses a standard sponge. The sponge absorbs liquid such as standard cleaning solutions for cleaning purposes, and also absorbs unwanted liquids such as juices from uncooked meat or chicken. The user generally rinses the sponge out in a sink and then stores the sponge in a dish or other standard flat surface. However, the sponge may still contain unwanted bacteria that have not been fully rinsed out by the user. Additionally, if the sponge has not been fully rinsed out, the moist sponge may be a breeding ground for mold and other forms of unwanted bacteria. One method of killing bacteria is to expose the item to UV light. UV light has proven to have a germicidal effect and is used in hospitals to help sanitize surgical instruments and other items which must be free from harmful bacteria. More recently, enclosures have been designed to house a UV light and personal hygiene items such as toothbrushes to more fully sanitize the brush or other item in between uses. However, none of the prior art addresses the unique issue of killing harmful bacteria that may be contained in a moist sponge.

BRIEF SUMMARY OF THE INVENTION

The primary object of the invention is to provide a sponge sanitizing enclosure that uses UV light to kill bacteria on or in a sponge.

Another object of the invention is to provide a sponge sanitizing enclosure that helps to press out remaining liquid from a sponge.

Another object of the invention is to provide a sponge sanitizing enclosure that is portable and needs no external power.

A further object of the invention is to provide a sponge for the sanitizing enclosure that is constructed of translucent material allowing UV light to pass completely through.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a sponge sanitizing enclosure comprising: a front cover, a rear cover, an inner back plate, a base housing, a push plate, a push button, a reflector plate, a UV lamp, electronics to support said UV lamp, a battery power supply, a translucent sponge, a hinge member, and a lamp cable, said front cover being dish shaped and said rear cover being dish shaped, said front cover and said rear cover facing each other forming a hollow housing and being joined at their base by said hinge member, said inner back plate forming a bisection of said front cover and said rear cover, said UV light centrally located between said rear cover and said inner back plate, said inner back plate having a centrally located aperture allowing said UV light to enter the space created by said inner back plate and said front cover, said front cover including a centrally located aperture, said push button fixedly attached to said push plate, said push button slidably engaged with said front cover aperture, the space between said push plate and said inner back plate sized to accommodate said translucent sponge, said hinge member terminating at its lower portion in said base housing, said electronics to support said UV lamp and said battery power supply contained within said base housing, said said electronics and said UV lamp electronically joined by said lamp cable.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
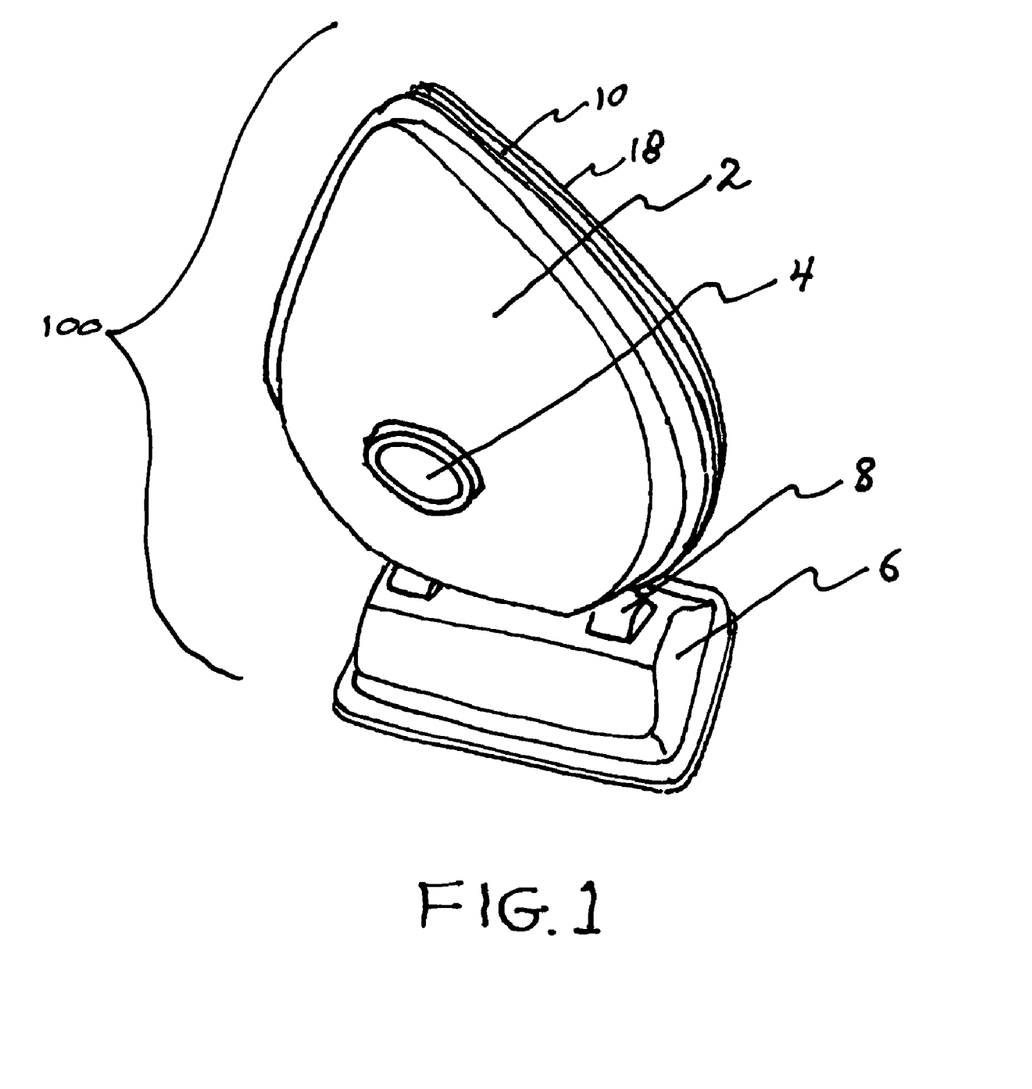
FIG. 1 is a front perspective view of the invention.

Referring now to FIG. 1 we see a front perspective view of the sanitary sponge enclosure of the present invention 100. The top portion is a housing that can contain a sponge and a UV light. Front cover 2 and push button 4 can easily be seen. The bottom portion 6 is a hollow base that contains electronics and a battery power supply for the UV light as will be described below. Front cover 2 is attached to base housing 6 by a hinge member 8. Translucent side strip 10 allows the user to see when the UV light is on.

Figure 2:
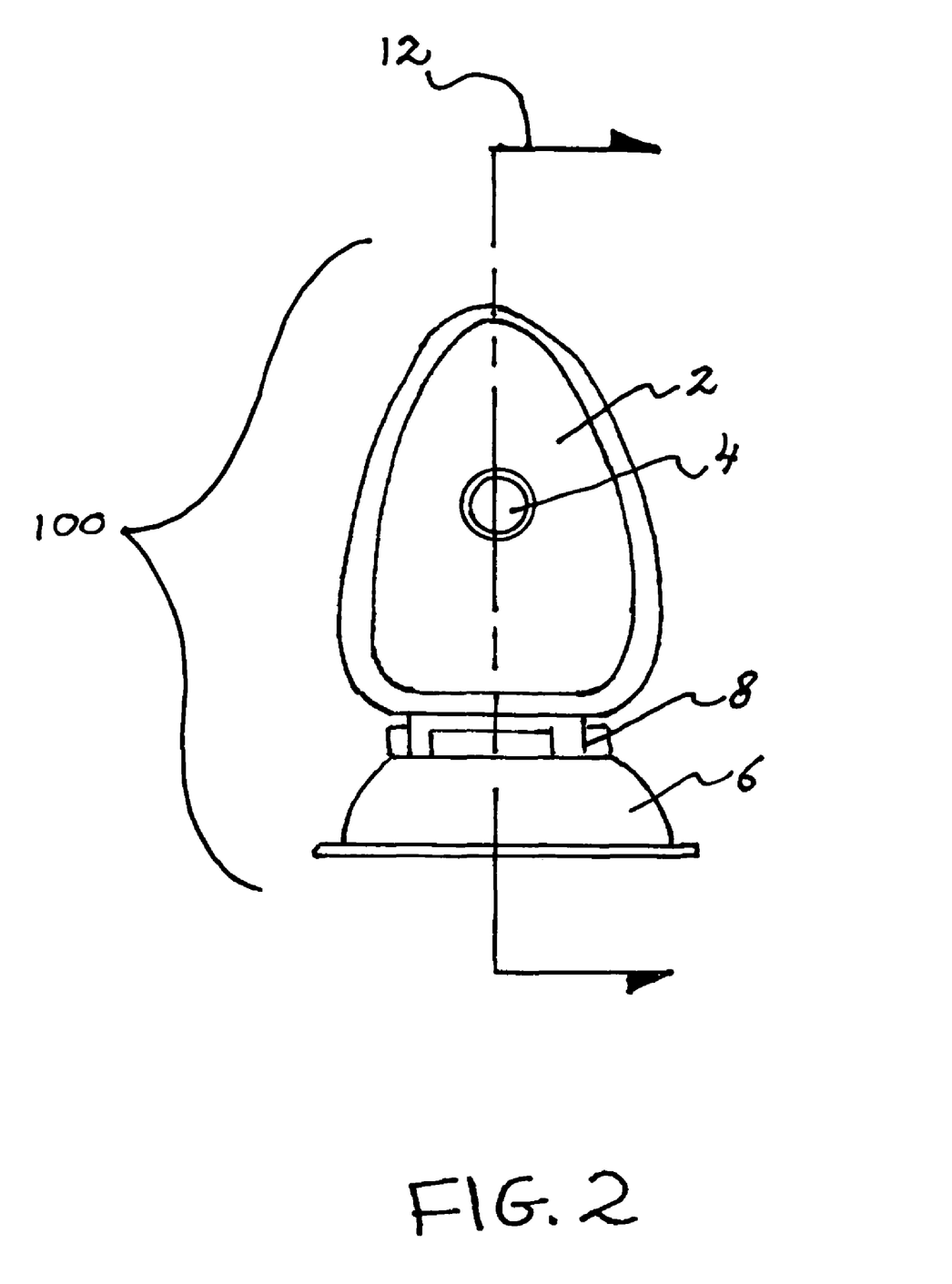
FIG. 2 is front plan view of the invention.

FIG. 2 is a front plan view of the invention 100. Hinge 8 can be more clearly seen in this view. A section line 12 defines the view shown in the section view shown in FIG. 4.

Figure 3:
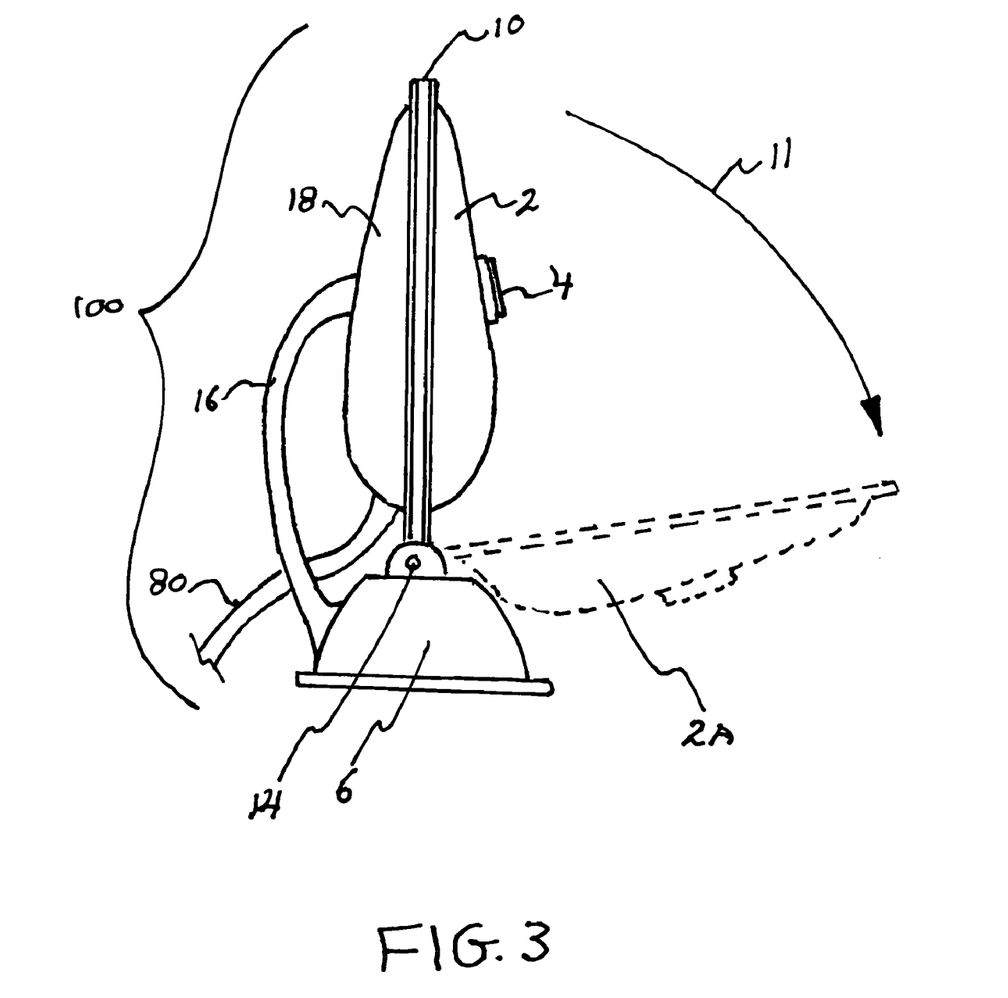
FIG. 3 is a side view of the invention.

FIG. 3 shows a side view of the invention and shows that the upper housing is formed of a front cover 2 and a rear cover 18. The two covers are dish shaped and face each other to form a hollow housing. The front cover 2 can be pivoted forward via hinge pin 14 as shown by radial direction line 11 and phantom view of front cover 2A. The rear cover 18 is fixedly held in place by rear cover support 16. Translucent strip 10 can be clearly seen. Push button 4 can be seen from the side. Drainage tube 80 allows excess water to exit the bottom or rear cover 18 and into a nearby sink.

Figure 4:
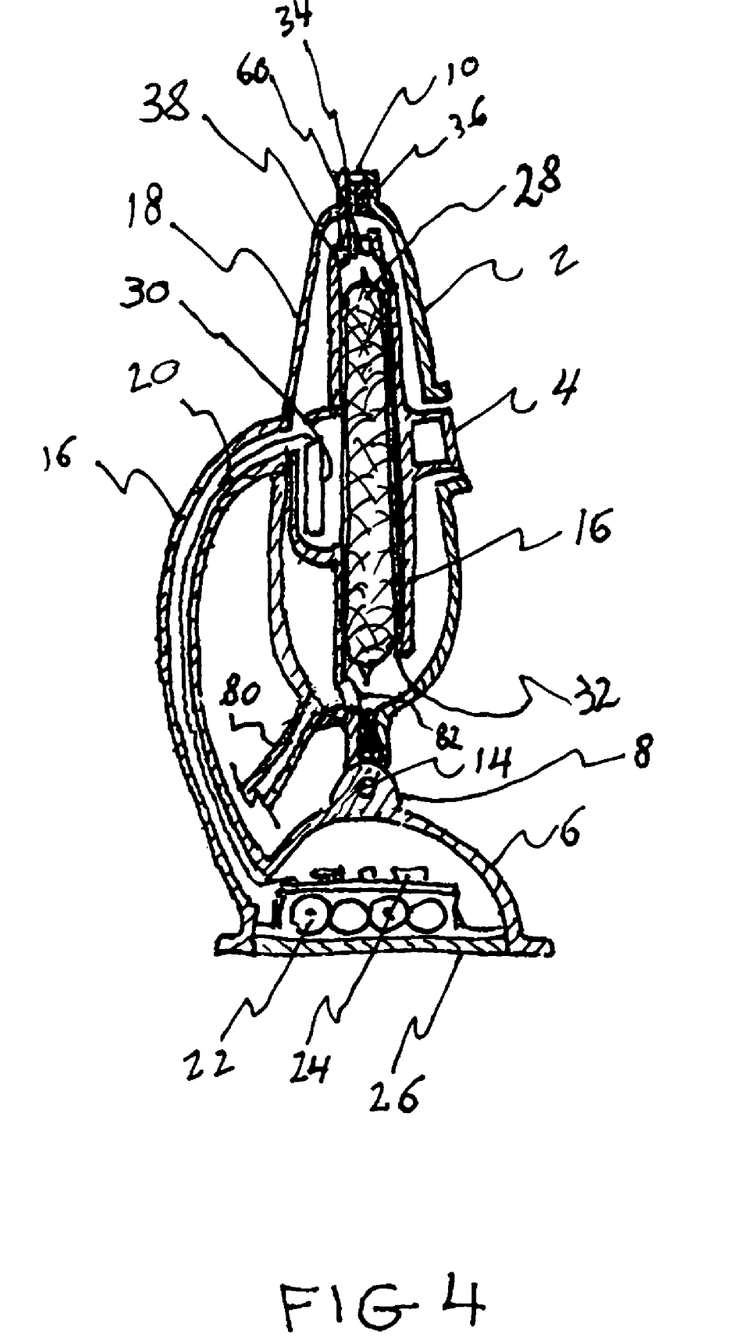
FIG. 4 is a side section view of the invention.

FIG. 4 is a side section view showing the interior construction of the present invention 100. Front cover 2 and rear cover 18 form a hollow housing. Inner back plate 38 bisects the inner area of the housing and includes a centrally located aperture that allows light from UV lamp 30 to pass through and make contact with the sponge 28 stored inside. Push button 4 is fixedly connected to push plate 16 so that when the user pushes on push button 4, push plate 16 the sponge 28 is squeezed between the push plate 16 and the inner back plate 38. Excess liquid can exit through an aperture in the inner back plate and out from an aperture and attached tube 80 at located at the bottom of rear cover 18. this squeezing action reduces the chance that excess moisture will remain in the sponge thereby reducing the possibility of mold or bacteria buildup due to moist conditions. A reflective panel 34 is fixedly mounted to the inner surface of push plate 16 so that UV light that penetrates sponge 28 can be reflected back into the sponge 28 for more complete UV exposure. The electronics 24 and battery power supply 22 needed to operate UV light 30 are contained in hollow base housing 6. Base plate 26 is removable and allows the user to replace batteries 22. An AC to DC socket, not shown, may be placed in the side wall of the base housing 6 so that the user can plug the unit 100 into a standard wall outlet. The two covers 2, 18 are removably held in place by standard means where the covers meet at the top portion. In the present embodiment a magnet 34 and a ferrous metal plate 36 provide the closure means.

When the user pushes on push button 4, the push plate is moved forward, and in the process activates switch 60 thereby turning on the UV light 30. A timer circuit in electronics portion 24 causes the light 30 to stay on for approximately ten seconds and then automatically turn off. Ten seconds has been shown to be a sufficient time to kill unwanted bacteria within the sponge 28. A voltage carrying cable 20 extends from the electronics portion 24, through the hollow interior of back cover support 16 and to UV lamp 30.

The sponge 28 is specially constructed of a translucent fibrous material. One such material is a three dimensional textile called "Space Flex" made by Pressless Company in Germany. The material is a translucent loop pile construction that interconnects with two textile planes creating an airy flexible material that has good scrubbing and cleanser retaining properties. Testing at LGA Laboratories in Nuremberg has shown that the resilient three dimensionality of the material is maintained even under conditions of intensive and long lasting stress. Obviously, a standard cellulose sponge material may be inserted in the enclosure of the present invention 100, however The translucent and airy quality of the unique material described above increases the ability of the UV light to penetrate the entire sponge and kill all harmful bacteria rather than just the bacteria on the surface of the sponge.

Figure 5:
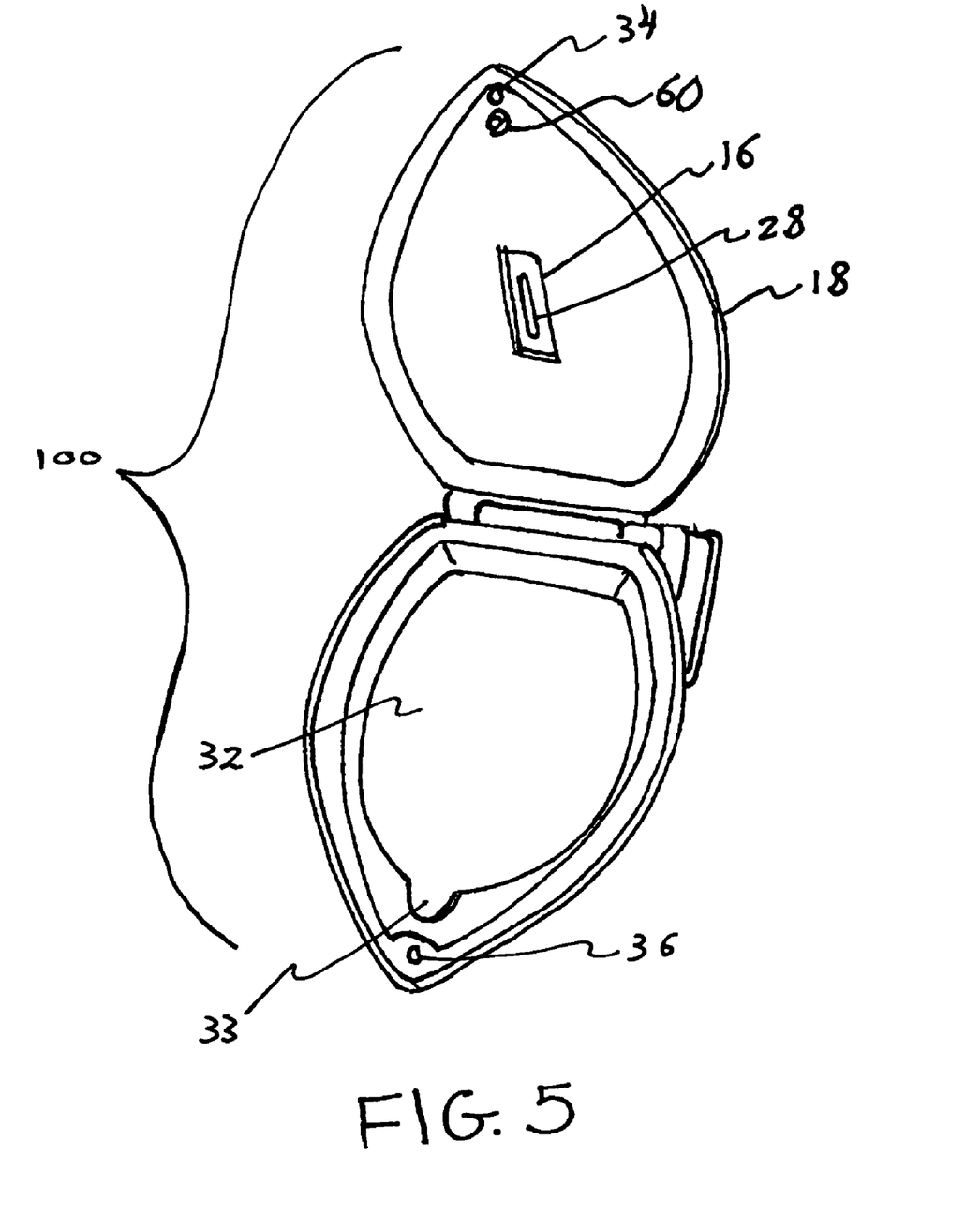
FIG. 5 is a perspective view of the invention in the open position.

FIG. 5 is a perspective view of the invention 10 in the open position. Reflective surface 32 is facing up and us mounted to push plate 16 located directly below the reflective plate 32. The tab 33 at the end of plate 32 can engage switch 60 when the unit 100 is closed and the user presses in on push button 4. This switch 60 turns on UV light 28 for ten seconds and then the light automatically turns off.

Figure 6:
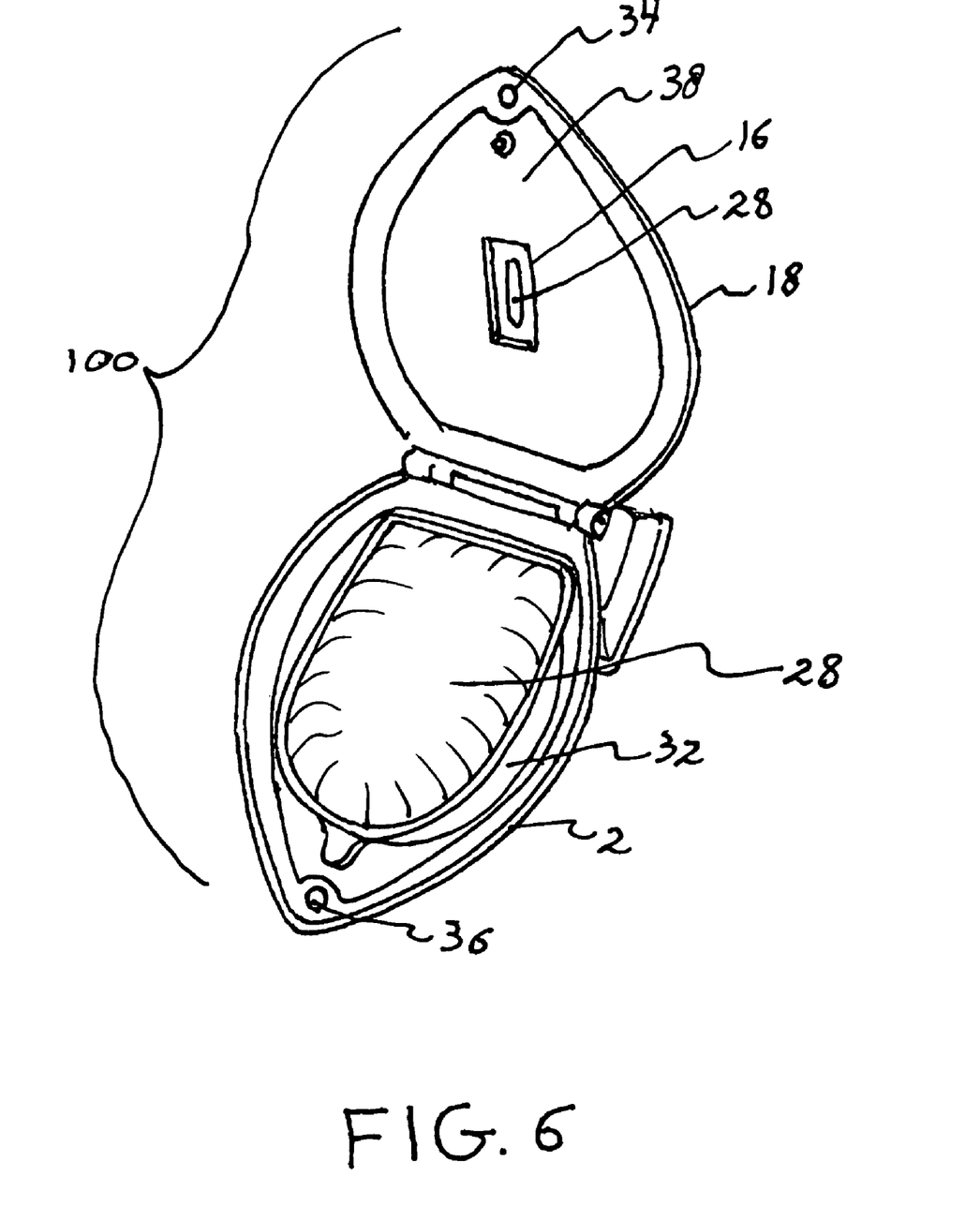
FIG. 6 is a perspective view of the invention in the open position with the sponge in place.

FIG. 6 shows the invention 100 in its open position with sponge 28 in place. The sponge is designed to fit snugly within top cover 2. After using the sponge 28, the user opens front cover 2 and swings it down to a horizontal position as shown. The user replaces the sponge 28 into front cover 2 and folds up the front cover 2 until the magnetic closure 34, 36 holds the two covers 2, 18 closed. The user then pushes in on push button 4 to both turn on UV light 28 and to squeeze out excess fluid from sponge 28.

Figure 7:
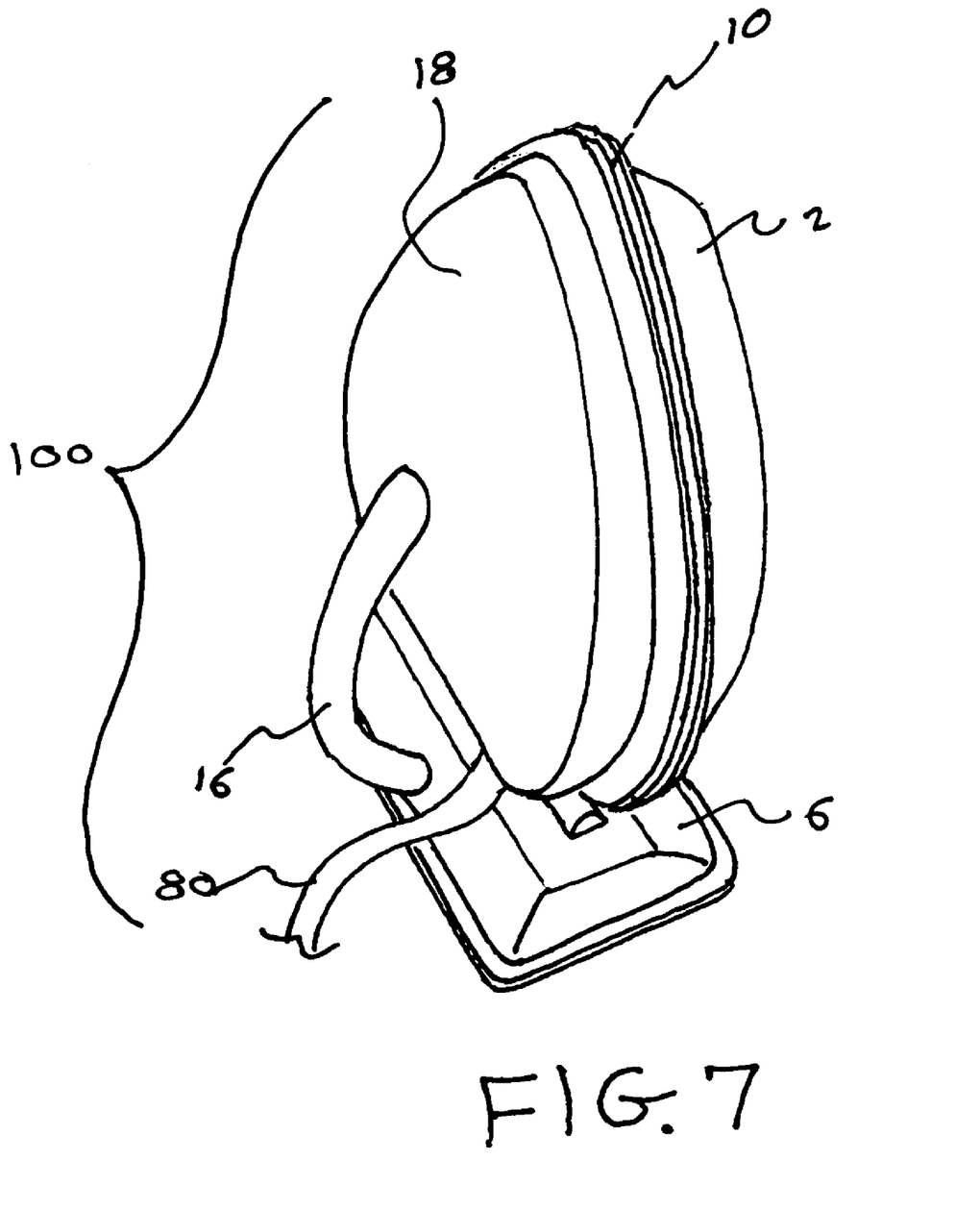
FIG. 7 is a rear perspective view of the invention.

FIG. 7 is a rear perspective view of the invention. Rear cover support 16 and drainage tube 80 can be clearly seen.

In the above described and illustrated way, a person can clean up liquids that may contain harmful bacteria and, by putting the special sponge 28 in the unique and novel storage device, can rid the sponge of harmful bacteria so that the sponge will be sanitary for the next use.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A sponge sanitizing enclosure comprising:
    a front cover;
    a rear cover;
    an inner back plate;
    a base housing;
    a push plate;
    a push button;
    a reflector plate;
    a UV lamp;
    electronics to support said UV lamp;
    a battery power supply;
    a translucent sponge;
    a hinge member; and
    a lamp cable;
    said front cover being dish shaped and said rear cover being dish shaped;
    said front cover and said rear cover facing each other forming a hollow housing and being joined at their base by said hinge member;
    said inner back plate forming a bi-section of said front cover and said rear cover;
    said UV light centrally located between said rear cover and said inner back plate;
    said inner back plate having a centrally located aperture allowing said UV light to enter the space created by said inner back plate and said front cover;
    said front cover including a centrally located aperture;
    said push button fixedly attached to said push plate;
    said push button slidably engaged with said front cover aperture;
    the space between said push plate and said inner back plate sized to accommodate said translucent sponge;
    said hinge member terminating at its lower portion in said base housing;
    said electronics to support said UV lamp and said battery power supply contained within said base housing;
    said electronics and said UV lamp electronically joined by said lamp cable.

2. A sponge sanitizing enclosure as claimed in claim 1 further comprising a reflector plate fixedly attached to said push plate that reflects UV light back into said translucent sponge.

3. A sponge sanitizing enclosure as claimed in claim 1 wherein said electronics includes a switch and a timing circuit that turns said UV light on for approximately ten seconds and then turns said UV light off.

4. A sponge sanitizing enclosure as claimed in claim 1 wherein said when a user presses in on said push button, said push plate causes said switch to activate as well as causing excess liquid in said sponge to be squeezed out.

5. A sponge sanitizing enclosure as claimed in claim 1 further comprising a drain hole located at the bottom of said rear cover and a flexible tube attached to said drain hole allowing said excess liquid to drain to a nearby sink.

6. A sponge sanitizing enclosure as claimed in claim 1 further comprising a releasable closure means that holds said front cover and said rear cover together until a user physically separates the two.

7. A sponge sanitizing enclosure as claimed in claim 1 further comprising an AC to DC adaptor socket built into said base housing allowing said UV electronics to be powered by standard house voltage.

* * * * *